US00PP31911P3

(12) United States Plant Patent
van Duijn

(10) Patent No.: US PP31,911 P3
(45) Date of Patent: Jun. 23, 2020

(54) ***LIGULARIA* PLANT NAMED 'LITTLE GOLDEN RAY'**

(50) Latin Name: *Ligularia dentata*
Varietal Denomination: Little Golden Ray

(71) Applicant: Jan Mark van Duijn, Lisse (NL)

(72) Inventor: Jan Mark van Duijn, Lisse (NL)

( * ) Notice: Subject to any disclaimer, the term of this patent is extended or adjusted under 35 U.S.C. 154(b) by 0 days.

(21) Appl. No.: 16/501,532

(22) Filed: Apr. 25, 2019

(65) Prior Publication Data

US 2020/0053939 P1 Feb. 13, 2020

(30) Foreign Application Priority Data

Aug. 7, 2018 (QZ) ..... PBR 20182053

(51) Int. Cl.
*A01H 5/02* (2018.01)
*A01H 6/14* (2018.01)

(52) U.S. Cl.
USPC ..... Plt./448
CPC ..... *A01H 6/14* (2018.05)

(58) Field of Classification Search
USPC ..... Plt./448
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Ligularia dentata* plant named 'Little Golden Ray' that is characterized by its compact plant habit with a short plant height, its foliage that is shiny and compact in size, and its small flowers.

2 Drawing Sheets

CROSS-REFERENCE TO RELATED APPLICATION

Priority is claimed to QZ PBR 2018/2053 for 'Little Golden Ray' filed Aug. 7, 2018, the entire contents of which are expressly incorporated herein by reference.

Botanical classification: *Ligularia dentata.*

Cultivar designation: 'Little Golden Ray'.

BACKGROUND OF THE INVENTION

The present invention relates to a new and distinct cultivar of *Ligularia dentata* and is hereinafter referred to by the cultivar name 'Little Golden Ray'.

The Inventor discovered the new cultivar in August of 2016 as a naturally occurring branch mutation of *Ligularia dentata* 'Osiris Fantaisie' (U.S. Plant Pat. No. 19,302) in a production field in HIllegom, The Netherlands.

Asexual reproduction of the new cultivar was first accomplished by tissue culture using meristematic tissue under direction of the Inventor in August of 2017 in Rijswijk, The Netherlands. Asexual reproduction of the new cultivar by division and tissue culture has shown that the unique features are stable and reproduced true to type in successive generations.

SUMMARY OF THE INVENTION

The following traits have been repeatedly observed and represent the characteristics of the new cultivar. These attributes in combination distinguish 'Little Golden Ray' as a new and unique cultivar of *Ligularia.*

1. 'Little Golden Ray' exhibits a compact plant habit with a short plant height.

2. 'Little Golden Ray' exhibits foliage that is shiny and compact in size.

3. 'Little Golden Ray' exhibits small flowers.

'Little Golden Ray' can be mostly closely compared to its parent plant 'Osiris Fantaisie'. 'Osiris Fantaisie' is similar to 'Little Golden Ray' in foliage coloration. 'Osiris Fantaisie' differs from 'Little Golden Ray' in having a much shorter plant height and in having larger leaves. 'Little Golden Ray' can also be compared to the *Ligularia* cultivars 'Osiris Café Noir' (U.S. Plant Pat. No. 21,351) and 'Othello' (not patented). 'Osiris Café Noir' is similar to 'Little Golden Ray' in having foliage that is similar in shape. 'Osiris Café Noir' differs from 'Little Golden Ray' in having foliage that emerges dark purple-black in color and in having flowers that are smaller in diameter. 'Othello' is similar to 'Little Golden Ray' in having similar flowers. 'Othello' differs from 'Little Golden Ray' in having a less compact plant habit, a much taller plant height, and foliage that is primarily green in color.

BRIEF DESCRIPTION OF THE DRAWINGS

The accompanying colored photographs illustrate the overall appearance and distinct characteristics of the new *Ligularia*. The photographs in the figures were taken of a 24-month-old plant that was field grown in Hillegom, The Netherlands and placed in a 29-cm container for the photographs.

The photograph in FIG. 1 provides a side view of 'Little Golden Ray' in bloom.

Figure 1:
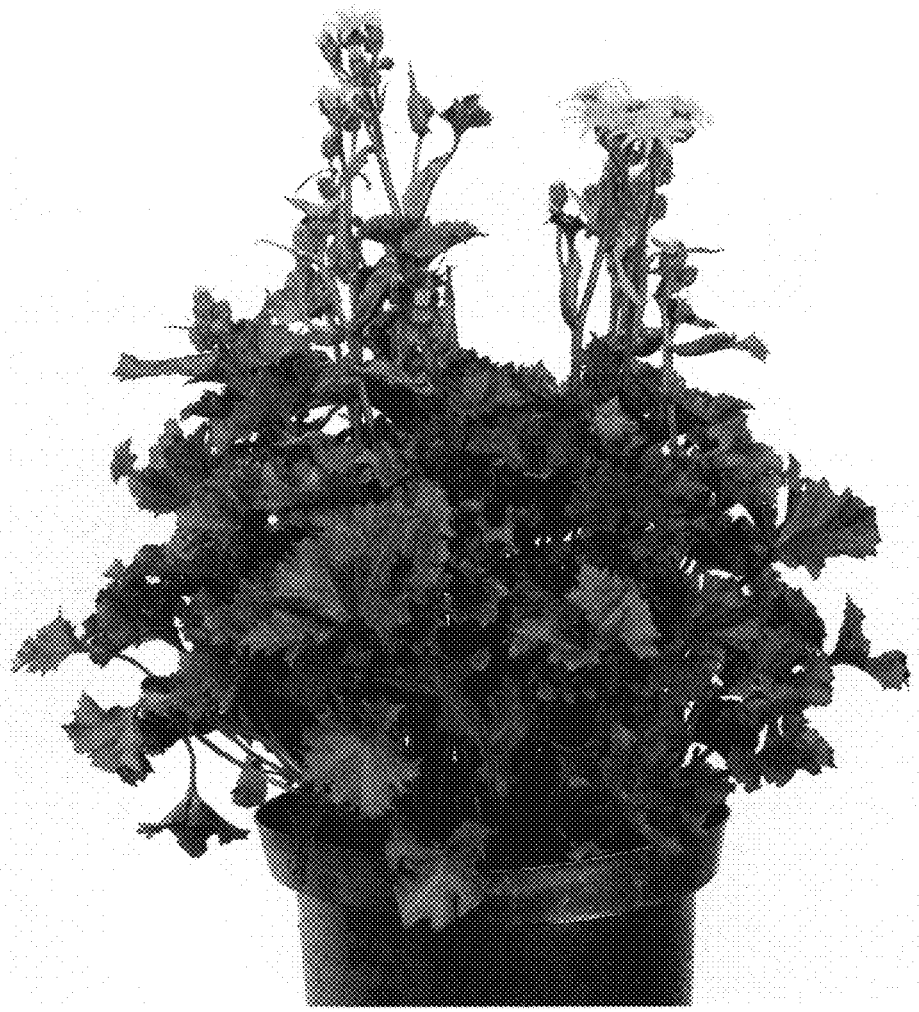
Figure 2:
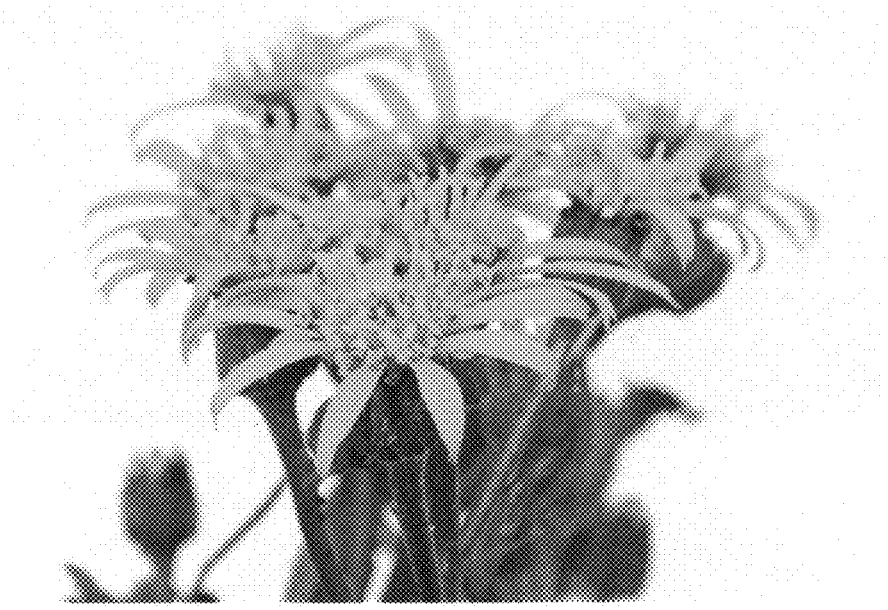

The photograph in FIG. 2 provides a close-up view of the inflorescences of 'Little Golden Ray'.

Figure 3:
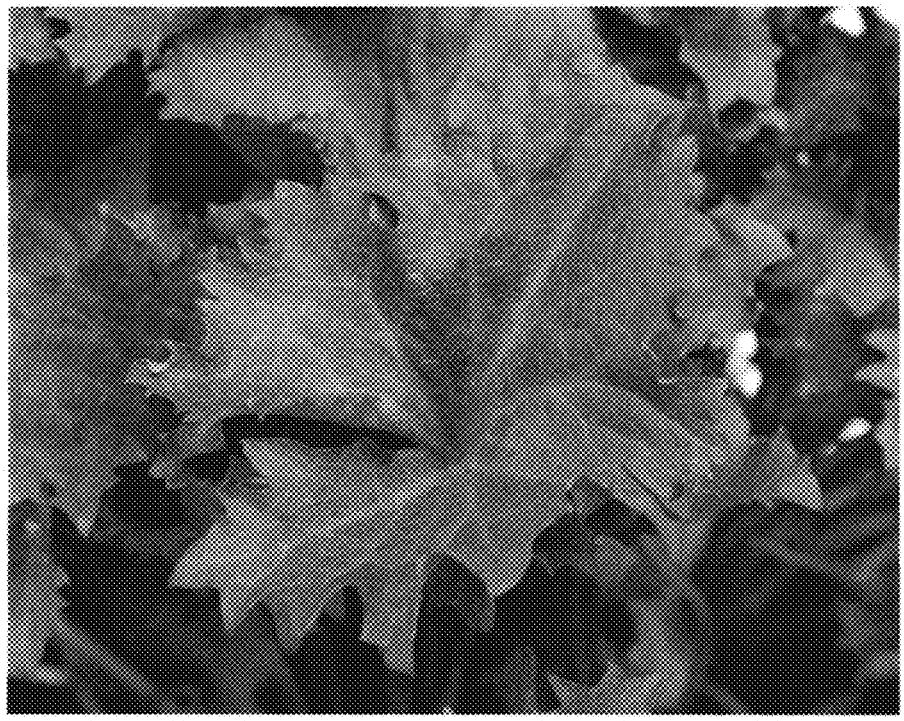

The photograph in FIG. 3 provides a close-up view of the foliage of 'Little Golden Ray'.

The colors in the photographs may differ slightly from the color values cited in the detailed botanical description, which accurately describe the colors of the new *Ligularia.*

DETAILED BOTANICAL DESCRIPTION OF THE PLANT

The following is a detailed description of 24-month-old plants of 'Little Golden Ray' that were field grown in Hillegom, The Netherlands. The phenotype of the new cultivar may vary with variations in environmental, climatic, and cultural conditions, as it has not been tested under all possible environmental conditions. The color determination is in accordance with the 2015 Colour Chart of The Royal Horticultural Society, London, England, except where general color terms of ordinary dictionary significance are used.

General description:

*Blooming habit.*—Blooms from July to September in The Netherlands.

*Plant type.*—Herbaceous perennial.

*Plant habit.*—Clump-forming, compact and dwarf.

*Height and spread.*—Reaches 45 to 50 cm in height and about 50 cm in spread as a mature plant in the landscape.

*Cold hardiness.*—At least to U.S.D.A. Zone 3.

*Diseases and pests.*—No susceptibility or resistance to diseases or pests has been observed.

*Root description.*—Fibrous.

*Branching habit.*—Basal stems, no lateral branches.

*Propagation.*—Tissue culture and division.

*Root development.*—An average of 6 to 8 weeks to root in a plug in tissue culture, and about 3 to 4 months to produce a young plant from a tissue culture plug.

*Growth rate.*—Moderate.

Stem description (flowering stems):

*Stem shape.*—Rounded and slightly angled.

*Stem color.*—146B and strongly tinged with N199A.

*Stem size.*—An average of 32.7 cm in length, 7 mm in diameter.

*Stem strength.*—Moderately strong.

*Stem aspect.*—Primary branches grow in an average angle of 5° to vertical stems (0°=vertical).

*Stem surface.*—Moderately pubescent with silky hairs an average of 1 mm in length and 161D in color.

*Stem number.*—Average of 16 basal branches.

*Internode length.*—Average of 145 cm in length.

*Branching.*—Main flowering stem grows from base.

Foliage description:

*Leaf shape.*—Reniform and moderately carinate.

*Leaf division.*—Simple.

*Leaf base.*—Hastate; lobes free to touching on basal leaves, lobes free on cauline leaves.

*Leaf apex.*—Acute.

*Leaf venation.*—Laciniate, color on upper surface 178B, color on lower surface 177B.

*Leaf margins.*—Coarsely dentate and strongly undulate.

*Leaf attachment.*—Petiolate.

*Leaf arrangement.*—Alternate.

*Leaf surface.*—(Both surfaces) smooth and glabrous and sparsely to moderately covered with very short hairs on veins; 0.5 mm in length and too fine to measure color.

*Leaf color.*—Young leaves upper surface; 137B, mature leaves lower surface; slightly darker than 148A, mature leaves upper surface; NN137A, young leaves lower surface; 200B and slightly tinged with 187B.

*Leaf size.*—Basal leaves; an average of 9.2 cm in length and 10.4 cm in width, cauline leaves; an average of 6.3 cm in length and 7.3 cm in width.

*Leaf quantity.*—Basal leaves continuously produced, an average of 3 cauline leaves per stem.

*Petioles.*—Oval in shape and sheathed at base on cauline leaves, basal leaves an average of 22.7 cm in length and 5 mm in width, cauline leaves an average of 14.6 cm in length and 3.5 mm in width with sheath; 5 cm in length and 1.2 cm in width, 146A to 146B in color, surface is sparsely covered with short silky hairs; average 1 mm in length and 161D in color.

Flower description:

*Inflorescence type.*—Terminal and axillary capitulum consisting of ray florets around disk florets.

*Capitulum number.*—An average of 12 per flowering stem, 200 per plant.

*Lastingness of inflorescence.*—An average of 2 weeks until senescence of ray florets, disk florets are persistent, terminal capitulum opens prior to axillary capitulum.

*Capitulum size.*—An average of 2.1 cm in depth and 4.3 cm in diameter, disk is an average of 1.5 cm in diameter.

*Capitulum angle.*—Terminal straight on top of main peduncle, axillary capitulum an average angle of 30° to main peduncle.

*Receptacle.*—Inverted triangular in shape, average of 3 mm in height and diameter, 145D in color.

*Fragrance.*—None.

*Phyllaries.*—An average of 12 arranged in a single row to form a campanulate involucre, average of 1.1 cm in length and 2 mm in width, fused at base with upper 18% free, acute apex, narrow oblong in shape, fused, color upper surface 146B with tip 200A, color lower surface a color between 146A and 148A but darker, tip and base tinged 183A, entire margin, upper surface glabrous and smooth and lower surface sparsely covered with short silky hairs; average of 1 mm in length and 161D in color.

*Flower buds.*—Broad ovate in shape, average of 1 cm in diameter and 1.3 cm in depth, 200C in color and tinged 178A with immature ray florets 14A.

*Peduncle.*—Branched, main peduncle; average of 7 cm in length (above last leaf) and 3 mm in width and held straight from stem, axillary peduncles; and an average of 2.7 cm in length and 3 mm in width and held at an average angle of 45° to stem, strong, 183A in color, surface sparsely covered with short silky hairs; average of 5 mm in length and 161D in color.

*Pedicels.*—None.

*Ray florets* (*sterile*).—Average of 12, tubular with lower 20% fused, oblanceolate in shape, vertical ridges on both surfaces, average of 2.5 cm in length and 3.5 mm in width, emarginated apex, narrow cuneate base, entire margin except apex, upper surface glabrous, matte and moderately velvety and slightly carinate, lower surface glabrous and slightly glossy and slightly carinate, initially held nearly vertical and become horizontal with tips reflexed as they mature, color of upper surface when opening and mature; 21A with tubular base 150D, color of lower surface when opening and mature; 21A and fading to 17C near base with tubular base 150D, pappus ring at base on top of ovary with hairs about 7 mm in length and 183C in color.

*Disk flowers* (*bisexual*).—Average of 60, tubular in shape, arranged spirally on receptacle, margin entire, base fused, apex acute, average of 2 cm in length and 4 mm in width, color when opening upper and lower surface; 16B and 166B at apex and 145D at base, color when fully open upper and lower surface; 18A and 150D at base, surface glabrous and matte on both surfaces, pappus ring at base on top of ovary with hairs about 7 mm in length and 183C in color, no spines.

Reproductive organs:

*Gynoecium.*—Pistil; 1, average of 1.3 cm in length, style; 1.1 cm in length, 145D in color, stigma; decurrent, 17B in color, ovary; 157D in color.

*Androecium.*—Stamens; 5, un-fused, coherent in cylinder around style, anthers; linear in shape, average of 4 mm in length, basifixed, 11A in color, filaments; 4 mm in length, 157D in color, pollen; moderate in quantity and 17C in color.

*Fruit/seed.*—No seeds observed to date.

It is claimed:

1. A new and distinct of *Ligularia* plant named 'Little Golden Ray' as herein illustrated and described.

* * * * *